United States Patent
Norsten et al.

(10) Patent No.: US 7,718,325 B2
(45) Date of Patent: May 18, 2010

(54) PHOTOCHROMIC MATERIAL, INKLESS REIMAGEABLE PRINTING PAPER, AND METHODS

(75) Inventors: Tyler B. Norsten, Oakville (CA); Gabriel Iftime, Mississauga (CA); Peter M. Kazmaier, Mississauga (CA)

(73) Assignee: Xerox Corporation, Norwalk, CT (US)

( * ) Notice: Subject to any disclaimer, the term of this patent is extended or adjusted under 35 U.S.C. 154(b) by 382 days.

(21) Appl. No.: 11/762,307

(22) Filed: Jun. 13, 2007

(65) Prior Publication Data

US 2008/0311495 A1    Dec. 18, 2008

(51) Int. Cl.
G03F 7/00    (2006.01)
G03F 7/004    (2006.01)

(52) U.S. Cl. .......... 430/19; 430/270.1; 430/270.15; 430/905; 430/945

(58) Field of Classification Search .......... 430/19, 430/270.1, 270.15, 905, 945
See application file for complete search history.

(56) References Cited

U.S. PATENT DOCUMENTS

| | | | |
|---|---|---|---|
| 3,825,427 A | 7/1974 | Inoue et al. |
| 3,877,941 A | 4/1975 | Lohmann |
| 3,961,948 A | 6/1976 | Saeva |
| 4,425,161 A | 1/1984 | Shibahashi et al. |
| 4,598,035 A | 7/1986 | Usami et al. |
| 4,659,649 A | 4/1987 | Dickinson et al. |
| 4,931,337 A | 6/1990 | Miyazaki et al. |
| 5,124,236 A | 6/1992 | Yamaguchi et al. |
| 5,262,280 A | 11/1993 | Knudsen et al. |
| 5,376,511 A | 12/1994 | Tatezono et al. |
| 5,458,874 A | 10/1995 | Pereira et al. |
| 5,677,107 A | 10/1997 | Neckers |
| 5,691,100 A | 11/1997 | Kudo et al. |
| 5,691,395 A | 11/1997 | Knudsen et al. |
| 5,710,420 A | 1/1998 | Martin et al. |
| 5,747,225 A | 5/1998 | Manico et al. |
| 6,067,185 A | 5/2000 | Albert et al. |
| 6,103,378 A | 8/2000 | Yao et al. |
| 6,200,646 B1 | 3/2001 | Neckers et al. |
| 6,528,221 B2 | 3/2003 | Takezawa et al. |
| 6,579,662 B1 | 6/2003 | Zheng et al. |
| 6,680,281 B2 | 1/2004 | Tajiri et al. |
| 6,761,758 B2 | 7/2004 | Boils-Boissier et al. |
| 6,866,981 B2 | 3/2005 | Furukawa et al. |
| 6,867,408 B1 | 3/2005 | Gu et al. |
| 6,906,118 B2 | 6/2005 | Goodbrand et al. |
| 7,018,714 B2 | 3/2006 | Kobayashi et al. |
| 7,057,054 B2 | 6/2006 | Irie et al. |
| 7,205,088 B2 | 4/2007 | Iftime et al. |
| 7,214,456 B2 | 5/2007 | Iftime et al. |
| 7,229,740 B2 | 6/2007 | Iftime et al. |
| 7,256,921 B2 | 8/2007 | Kumar et al. |
| 7,332,257 B2 | 2/2008 | Miyako et al. |
| 7,381,506 B2 | 6/2008 | Iftime et al. |
| 7,441,887 B2 | 10/2008 | Senga et al. |
| 2002/0160318 A1 | 10/2002 | Richter et al. |
| 2003/0130456 A1 | 7/2003 | Kim et al. |
| 2005/0012998 A1 | 1/2005 | Kumar et al. |
| 2005/0244744 A1 | 11/2005 | Kazmaier et al. |
| 2005/0269556 A1 | 12/2005 | Evans et al. |
| 2006/0001944 A1 | 1/2006 | Chopra et al. |
| 2006/0222972 A1 | 10/2006 | Chopra et al. |
| 2006/0222973 A1 | 10/2006 | Iftime et al. |
| 2006/0236470 A1 | 10/2006 | Sabnis et al. |
| 2006/0251988 A1 | 11/2006 | Iftime et al. |
| 2006/0257785 A1 | 11/2006 | Johnson |
| 2007/0054215 A1 | 3/2007 | Iftime et al. |
| 2007/0072110 A1 | 3/2007 | Iftime et al. |
| 2007/0112103 A1 | 5/2007 | Zhou et al. |

FOREIGN PATENT DOCUMENTS

| | | |
|---|---|---|
| CA | 2 053 094 A1 | 4/1992 |
| DE | 2906193 A * | 8/1980 |
| EP | 1 367 111 | 12/2003 |
| EP | 1 405 891 | 4/2004 |
| EP | 1 591 829 | 11/2005 |
| EP | 1 591 831 | 11/2005 |
| FR | 2774998 | 8/1999 |
| GB | 2 430 257 | 3/2007 |
| JP | 57-136645 | 8/1982 |
| JP | A-61-175087 | 8/1986 |
| JP | A-5-265129 | 10/1993 |
| JP | A-11-30835 | 2/1999 |
| JP | 11322739 A * | 11/1999 |

(Continued)

OTHER PUBLICATIONS

Babeshko et al., "Spior-2H-oxocines", Khimiya Geterotsikicheskikh Soedinenii, No. 11, pp. 1490-1492, Nov. 1976.*

(Continued)

*Primary Examiner*—Amanda C. Walke
(74) *Attorney, Agent, or Firm*—Oliff & Berridge, PLC

(57) ABSTRACT

An image forming medium includes a substrate and an imaging layer coated on or impregnated into said substrate, where the imaging layer includes as a photochromic material a spiropyran compound having a conjugated pathway, dispersed in a polymeric binder, wherein the photochromic material exhibits a reversible transition between a colorless state and a colored state in response to heat and light.

23 Claims, No Drawings

FOREIGN PATENT DOCUMENTS

| | | | |
|---|---|---|---|
| JP | 2000256347 A | * | 9/2000 |
| JP | A-2002-179672 | | 6/2002 |
| JP | A-2002-240441 | | 8/2002 |
| JP | A-2002-285146 | | 10/2002 |
| JP | A-2003-255489 | | 9/2003 |
| JP | A-2003-255490 | | 9/2003 |
| JP | A-2004-039009 | | 2/2004 |
| JP | A-2004-045037 | | 2/2004 |
| JP | A-2004-091638 | | 3/2004 |
| JP | A-2004-149501 | | 5/2004 |
| JP | A-2004-256780 | | 9/2004 |
| JP | A-2005-082507 | | 3/2005 |
| JP | A-2005-250463 | | 9/2005 |
| WO | WO 97/31033 | | 8/1997 |
| WO | WO 00/16985 A1 | | 3/2000 |
| WO | WO 2006/039130 A1 | | 4/2006 |
| WO | WO 2007/105699 A1 | | 9/2007 |
| WO | WO 2008/043853 A2 | | 4/2008 |

OTHER PUBLICATIONS

Mandel et al., "Titanocene(III) mediated radical cyclizations of epoxides for the synthesis of medium-sized cyclic ethers", Tetrahedron 63 (2007). pp. 11341-11348.*
M. Irie, "Diarylethense for Memories and Switches," Chem Reviews, 100, pp. 1685-1716 (2000).
Kentaro Morimitsu et al., "Dithienylethenes With a Novel Photochromic Performance," J. Org. Chem., vol. 67, pp. 4574-4578 (2002).
"Dolch Introduces World's First Ruggedized Notebook with Integrated Printer" available at http://news.thomasnet.com/fullstory/ 7005/447, pp. 1-4, Feb. 6, 2002.
Masamitsu Shirai et al., "Photoacid and Photobase Generators: Chemistry and Applications to Polymeric Materials," *Prog. Polym. Sci*. vol. 21, pp. 1-45 (1996).
T. Hirose et al., "Self-Assembly of Photochromic Diarylethenes With Amphiphilic Side Chains: Reversible Thermal and Photochemical Control," J. Org. Chem., 71, pp. 7499-7508 (2006).
T. Norsten et al., "Photoregulation of Fluorescence in a Porphyrinic Dithienylethene Photochrome," J. Am. Chem. Soc., 123(8), pp. 1784-1785 (2001).
Vladimir I. Minkin, "Photo-, Thermo-, Solvato-, and Electrochromic Spiroheterocyclic Compounds," Chemical Reviews, 104, 5, pp. 2751-2776 (2004).
Takayuki Suzuki et al., "Stabilization of the merocyanine form of photochromic compounds in fluoro alcohols is due to a hydrogen bond", Chem. Commun., 2685-2686 (1998).
Ronald F.M. Lange et al., "Supramolecular polymer interactions based on the alternating copolymer of styrene and Maleimide" Macromolecules, 28, 782-783 (1995).
Vladimir I. Minkin et al., "Perimidine spirocyclohexa dienones" in Organic Photochromic and Thermochromic Compounds, VI, Plenum Press, pp. 315-340 (1999).
John Biteau et al., "Photochromism of Spirooxazine-Doped Gels," J. Phys. Chem., 100, 9024-9031 (1996).
Leonard J. Prins et al., "Noncovalent Synthesis Using Hydrogen Bonding," Angew. Chem. Int. Ed., 40, 2382-2426 (2001).
Wojtyk et al., "Effects of metal ion complexation on the spiropyran-merocyanine interconversion: development of a thermally stable photo-switch," J. Chem. Soc. Chem, Comm., pp. 1703-1704, 1998.
Kentaro Morimitsu et al., "Thermal Cycloreversion Reaction of a Photochromic Dithienylperfluorocyclopentene with *tert*-Butoxy Substituents at the Reactive Carbons," The Chemical Society of Japan, 2002, p. 572-573.
Terry M. Cresp et al., "A Synthesis of $\alpha\beta$-Unsaturated Aldehydes," J. Chem. Soc., Perkin Trans., 1, pp. 37-41 (1974).
Elliot Berman et al., "Photochromic Spiropyrans. 1. The Effect of Substituents on the Rate of Ring Closure," J. Am. Chem. Soc., 81, 5605-5608 (1959).
Sheng-Hua Liu et al., "Synthesis of Negative Photochromic Crowned Spirobenzopyrans," Syn. Commun., 30, 5, 895-902 (2000).
Yu M. Chunaev et al., "Reaction of the Fischer Base With Nitro- and Bromo-Substituted $\alpha$Hydroxycinnamaldehydes," Chem. Heterocycl. Compd., 628-631 (1984).
U.S. Appl. No. 11/762,152, filed Jun. 13, 2007, to Iftime et al.
U.S. Appl. No. 11/762,327, filed Jun. 13, 2007, to Iftime et al.
U.S. Appl. No. 11/762,147, filed Jun. 13, 2007, to Iftime et al.
U.S. Appl. No. 11/762,098, filed Jun. 13, 2007, to Iftime et al.
U.S. Appl. No. 11/762,157, filed Jun. 13, 2007, to Iftime et al.
U.S. Appl. No. 11/762,153, filed Jun. 13, 2007, to Iftime et al.
U.S. Appl. No. 11/762,144, filed Jun. 13, 2007, to Kazmaier et al.
U.S. Appl. No. 11/762,150, filed Jun. 13, 2007, to Norsten et al.
U.S. Appl. No. 11/762,107, filed Jun. 13, 2007, to Iftime et al.
U.S. Appl. No. 11/762,176, filed Jun. 13, 2007, to Norsten et al.
U.S. Appl. No. 11/762,307, filed Jun. 13, 2007, to Norsten et al.
U.S. Appl. No. 11/762,159, filed Jun. 13, 2007, to Kazmaier et al.
U.S. Appl. No. 11/762,311, filed Jun. 13, 2007, to Kazmaier et al.
Sep. 9, 2009 European Office Action issued in European Application No. 08 155 983.3-1217.
Dec. 22, 2009 Office Action issued in U.S. Appl. No. 11/762,176.

* cited by examiner

PHOTOCHROMIC MATERIAL, INKLESS REIMAGEABLE PRINTING PAPER, AND METHODS

TECHNICAL FIELD

This disclosure is generally directed to a photochromic material, a substrate, methods, and apparatus for inkless printing on reimagable paper. More particularly, in embodiments, this disclosure is directed to improved photochromic materials having conjugated pathways for increased thermal stability. In other in embodiments, this disclosure is directed to an inkless reimagable printing substrate, such as inkless printing paper utilizing a composition that is imagable and erasable by heat and light, such as comprising as a photochromic material a spiropyran compound having a conjugated pathway, dispersed in a polymeric binder, wherein the photochromic material exhibits a reversible transition between a colorless state and a colored state in response to heat and light. Imaging is conducted by applying UV light to the imaging material to cause a color change, and erasing is conducted by applying visible light and/or heat to the imaging material to reverse the color change. Other embodiments are directed to inkless printing methods using the inkless printing substrates, and apparatus and systems for such printing.

CROSS-REFERENCE TO RELATED APPLICATIONS

Disclosed in commonly assigned U.S. patent application Ser. No. 11/123,163, filed May 6, 2005, is an image forming medium, comprising a polymer, a photochromic compound containing chelating groups embedded in the polymer, and a metal salt, wherein molecules of the photochromic compound are chelated by a metal ion from the metal salt.

Disclosed in commonly assigned U.S. patent application Ser. No. 10/835,518, filed Apr. 29, 2004, is an image forming method comprising: (a) providing a reimagable medium comprised of a substrate and a photochromic material, wherein the medium is capable of exhibiting a color contrast and an absence of the color contrast; (b) exposing the medium to an imaging light corresponding to a predetermined image to result in an exposed region and a non-exposed region, wherein the color contrast is present between the exposed region and the non-exposed region to allow a temporary image corresponding to the predetermined image to be visible for a visible time; (c) subjecting the temporary image to an indoor ambient condition for an image erasing time to change the color contrast to the absence of the color contrast to erase the temporary image without using an image erasure device; and (d) optionally repeating procedures (b) and (c) a number of times to result in the medium undergoing a number of additional cycles of temporary image formation and temporary image erasure.

Disclosed in commonly assigned U.S. patent application Ser. No. 10/834,722, filed Apr. 29, 2004, is a reimagable medium comprising: a substrate; and a photochromic material, wherein the medium is capable of exhibiting a color contrast and an absence of the color contrast, wherein the medium has a characteristic that when the medium exhibits the absence of the color contrast and is then exposed to an imaging light corresponding to a predetermined image to result in an exposed region and a non-exposed region, the color contrast is present between the exposed region and the non-exposed region to form a temporary image corresponding to the predetermined image that is visible for a visible time, wherein the medium has a characteristic that when the temporary image is exposed to an indoor ambient condition for an image erasing time, the color contrast changes to the absence of the color contrast to erase the temporary image in all of the following: (i) when the indoor ambient condition includes darkness at ambient temperature, (ii) when the indoor ambient condition includes indoor ambient light at ambient temperature, and (iii) when the indoor ambient condition includes both the darkness at ambient temperature and the indoor ambient light at ambient temperature, and wherein the medium is capable of undergoing multiple cycles of temporary image formation and temporary image erasure.

Disclosed in commonly assigned U.S. patent application Ser. No. 11/220,803, filed Sep. 8, 2005, is an image forming medium, comprising: a substrate; and an imaging layer comprising a photochromic material and a polymer binder coated on said substrate, wherein the photochromic material exhibits a reversible homogeneous-heterogeneous transition between a colorless state and a colored state in the polymer binder.

Disclosed in commonly assigned U.S. patent application Ser. No. 11/220,572, filed Sep. 8, 2005, is an image forming medium, comprising: a substrate; and a mixture comprising a photochromic material and a solvent wherein said mixture is coated on said substrate, wherein the photochromic material exhibits a reversible homogeneous-heterogeneous transition between a colorless state and a colored state in the solvent.

Disclosed in commonly assigned U.S. patent application Ser. No. 11/123,163, filed May 6, 2005, is an image forming medium, comprising a polymer; and a photochromic compound containing chelating groups embedded in the polymer; and a metal salt; wherein molecules of the photochromic compound are chelated by a metal ion from the metal salt.

Disclosed in commonly assigned U.S. patent application Ser. No. 11/093,993, filed Mar. 20, 2005, is a reimagable medium, comprising: a substrate having a first color; a photochromic layer adjacent to the substrate; a liquid crystal layer adjacent to the photochromic layer, wherein the liquid crystal layer includes a liquid crystal composition; and an electric field generating apparatus connected across the liquid crystal layer, wherein the electric field generating apparatus supplies a voltage across the liquid crystal layer.

Disclosed in commonly assigned U.S. patent application Ser. No. 10/834,529, filed Apr. 29, 2004, is a reimagable medium for receiving an imaging light having a predetermined wavelength scope, the medium comprising: a substrate; a photochromic material capable of reversibly converting among a number of different forms, wherein one form has an absorption spectrum that overlaps with the predetermined wavelength scope; and a light absorbing material exhibiting a light absorption band with an absorption peak, wherein the light absorption band overlaps with the absorption spectrum of the one form.

The entire disclosure of the above-mentioned applications are totally incorporated herein by reference.

BACKGROUND

Inkjet printing is a well-established market and process, where images are formed by ejecting droplets of ink in an image-wise manner onto a substrate. Inkjet printers are widely used in home and business environments, and particularly in home environments due to the low cost of the inkjet printers. The inkjet printers generally allow for producing high quality images, ranging from black-and-white text to photographic images, on a ride range of substrates such as standard office paper, transparencies, and photographic paper.

However, despite the low printer costs, the cost of replacement inkjet cartridges can be high, and sometimes higher than the cost of the printer itself. These cartridges must be replaced frequently, and thus replacement costs of the ink cartridges is a primary consumer complaint relating to inkjet printing. Reducing ink cartridge replacement costs would thus be a significant enhancement to inkjet printing users.

In addition, many paper documents are promptly discarded after being read. Although paper is inexpensive, the quantity of discarded paper documents is enormous and the disposal of these discarded paper documents raises significant cost and environmental issues. Accordingly, there is a continuing desire for providing a new medium for containing the desired image, and methods for preparing and using such a medium. In aspects thereof it would be desirable to be reusable, to abate the cost and environmental issues, and desirably also is flexible and paper-like to provide a medium that is customarily acceptable to end-users and easy to use and store.

Although there are available technologies for transient image formation and storage, they generally provide less than desirable results for most applications as a paper substitute. For example, alternative technologies include liquid crystal displays, electrophoretics, and gyricon image media. However, these alternative technologies may not in a number of instances provide a document that has the appearance and feel of traditional paper, while providing the desired reimageability.

Imaging techniques employing photochromic materials, that is materials which undergo reversible or irreversible photoinduced color changes are known, for example, U.S. Pat. No. 3,961,948 discloses an imaging method based upon visible light induced changes in a photochromic imaging layer containing a dispersion of at least one photochromic material in an organic film forming binder.

These and other photochromic (or reimagable or electric) papers are desirable because they can provide imaging media that can be reused many times, to transiently store images and documents. For example, applications for photochromic based media include reimagable documents such as, for example, electronic paper documents. Reimagable documents allow information to be kept for as long as the user wants, then the information can be erased or the reimagable document can be re-imaged using an imaging system with different information.

Although the above-described approaches have provided reimagable transient documents, there is a desire for reimagable paper designs that provide longer image life-times, and more desirable paper-like appearance and feel. For example, while the known approaches for photochromic paper provide transient visible images, the visible images are very susceptible to UV, such as is present in both ambient interior light and more especially in sun light, as well as visible light. Due to the presence of this UV and visible light, the visible images are susceptible to degradation by the UV light, causing the unimaged areas to darken and thereby decrease the contrast between the desired image and the background or unimaged areas.

That is, a problem associated with transient documents is the sensitivity of the unimaged areas to ambient UV-VIS light (such as <420 nm) where the photochromic molecule absorbs. Unimaged areas become colored after a period of time, decreasing the visual quality of the document, because the contrast between white and colored state is reduced. One approach, described in the above-referenced U.S. patent application Ser. No. 10/834,529, is to stabilize the image against light of wavelength<420 nm by creating a band-pass window for the incident light capable of isomerising (i.e. inducing coloration) in the material, centered around 365 nm. However, the unimaged areas of the documents still are sensitive to UV-VIS light of wavelength centered around 365 nm.

Another problem generally associated with known transient documents is that common photochromic materials such as merocyanines (the colored state isomer form of spiropyrans) are not significantly stable over time to ambient heat and light, and thus tend to revert back to the colorless state through both thermal and visible light.

SUMMARY

It is desirable for some uses that an image formed on a reimagable medium such as a transient document remains stable for extended time periods, without the image or image contrast being degraded by exposure to ambient UV light. However, it is also desired that the image can be erased when desired, to permit reimaging of the medium. It is also desired that the imaging medium be similar to conventional paper, that is, having the look and feel of conventional paper. This generally requires that the imaging composition of the imaging medium be a solid layer, not a layer of a solvent-based system. Electronic paper documents should also maintain a written image for as long as the user needs to view it, without the image being degraded by ambient heat or light. The image may then be erased or replaced with a different image by the user on command.

Common merocyanines (the spiropyran isomer responsible for creating image contrast in some current transient documents) are not significantly stable and revert back to the colorless state through both thermal and visible light. The usefulness of such documents could be increased if the stability of the isomer was more stable, particularly against ambient heat and light. It has been discovered that this increased stability can be provided by introducing a conjugated pathway into the molecule. The conjugated pathway introduces the formation of additional isomeric forms of the colored state compound, which are more stable than conventional photochromic materials. This creates a thermally and/or photochemically stable image. The resulting image can be erased by reversing the isomerization changes through the application of thermal energy (heat) and the colored state can be driven back to the noncolored state both thermally and/or with visible light.

The present disclosure addresses these and other needs, in embodiments, by providing improved photochromic materials, such as modified spiropyrans/merocyanines having a conjugated pathway, that exhibit increased thermal stability. The present disclosure also provides, in embodiments, a reimagable image forming medium utilizing a composition that is both imagable and erasable by heat and light, and which comprises an imaging composition that comprises as a photochromic material a spiropyran compound having a conjugated pathway, dispersed in a polymeric binder, wherein the photochromic material exhibits a reversible transition between a colorless state and a colored state in response to heat and light. Imaging is conducted by applying UV light to the imaging material to cause a color change, and erasing is conducted by applying visible light and optionally heat to the imaging material to reverse the color change. The present disclosure in other embodiments provides an inkless printing method using the reimagable inkless printing substrates, and apparatus and systems for such printing.

The present disclosure thereby provides a printing media, method, and printer system for printing images without using ink or toner. The paper media has a paper-like look and feel and carries a special imagable composition and it is printed and can be erased with light and/or heat. The paper media thus allows image formation and erasure using a printer that does not require ink or toner replacement, and instead images the paper using a UV light source, such as a LED.

In an embodiment, the present disclosure provides a photochromic compound having a conjugated pathway, the photochromic compound having the formula (1), (2), or (3):

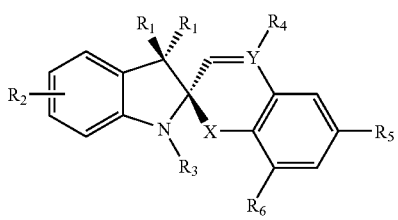

(1)

wherein:

each of $R_1$-$R_6$ independently represents a group selected from the group consisting of hydrogen, alkyl, aryl, arylalkyl, silyl, nitro, cyano, halide atoms, amine, hydroxyl, alkoxy, aryloxy, alkylthio, arylthio, aldehyde, ketone, ester, amide, carboxylic acid, and sulfonic acid, wherein the alkyl, aryl, and arylalkyl groups can optionally be substituted with one or more groups selected from the group consisting of silyl groups, nitro groups, cyano groups, halide atoms, amine groups, hydroxy groups, alkoxy groups, aryloxy groups, alkylthio groups, arylthio groups, aldehyde groups, ketone groups, ester groups, amide groups, carboxylic acid groups, and sulfonic acid groups, X is a heteroatom selected from the group consisting of N, O, and S, and Y represents an alkene group of from 3 to about 15 carbon atoms and provides at least one conjugated double bond to the double bond of the parent molecule;

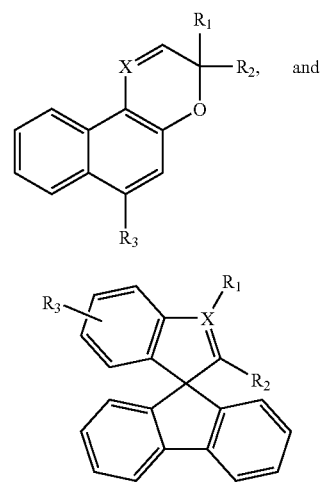

where each of $R_1$, $R_2$, and $R_3$ are defined as above, and X in formulae (2) and (3) is an alkene group of from 3 to about 15 carbon atoms and provides at least one conjugated double bond to the double bond of the parent molecule.

In an embodiment, the present disclosure provides a reimagable image forming medium, comprising a substrate; and an imaging layer coated on or impregnated into said substrate, wherein the imaging layer comprises as a photochromic material a spiropyran compound having a conjugated pathway, dispersed in a polymeric binder, wherein the photochromic material exhibits a reversible transition between a colorless state and a colored state in response to heat and light.

In another embodiment, the present disclosure provides a method of making a reimagable image forming medium, comprising applying an imaging layer composition to a substrate, wherein the imaging layer comprises as a photochromic material a spiropyran compound having a conjugated pathway, dispersed in a polymeric binder, wherein the photochromic material exhibits a reversible transition between a colorless state and a colored state in response to heat and light.

In another aspect, the present disclosure provides a method of forming an image, comprising:

providing an image forming medium comprising:

a substrate; and an imaging layer coated on or impregnated into said substrate, wherein the imaging layer comprises as a photochromic material a spiropyran compound having a conjugated pathway, dispersed in a polymeric binder; and exposing the image forming medium to UV irradiation of a first wavelength in an imagewise manner, wherein the photochromic material exhibits a reversible transition between a colorless state and a colored state in response to heat and light.

The imaging method can be conducted, for example, using an imaging system, comprising:

the above image forming medium; and a printer comprising two irradiation sources, wherein one irradiation source sensitizes the photochromic material to convert the photochromic material from a colorless state to a colored state the other irradiation source converts the photochromic material from a colored state to a colorless state.

DETAILED DESCRIPTION OF EXEMPLARY EMBODIMENTS

Generally, in various exemplary embodiments, there is provided an inkless reimagable paper or image forming medium formed using a composition that is imagable and erasable by heat and light, such as comprising as a photochromic material a spiropyran compound having a conjugated pathway, dispersed in a polymeric binder, wherein the photochromic material exhibits a reversible transition between a colorless state and a colored state in response to heat and light. Exposing the imaging layer to UV light causes the photochromic material to easily convert from the colorless state to a stable colored state through several isomeric forms. The final isomer form, due to the extended double bond conjugation, stabilizes the merocyanine form of the photochromic material, and thus stabilizes the colored state when the light is removed. Likewise, exposing the imaging layer to visible light and optional heat initiates the reverse isomerization process and converts the photochromic material back from the colored state to the colorless state. The composition thus exhibits a reversible transition between a clear state and a colored state in the image forming medium. By a colored state, in embodiments, refers to for example, the presence of visible wavelengths; likewise, by a colorless state, in embodiments, refers to for example, the complete or substantial absence of visible wavelengths.

Photochromism and thermochromism are defined as the reversible photocoloration of a molecule from exposure to light (electromagnetic radiation) and heat (thermal radiation) based stimuli respectively. Typically photochromic molecules undergo structural and/or electronic rearrangements when irradiated with UV light that converts them to a more conjugated colored state. In the case of purely photochromic molecules, the colored state can typically be converted back to their original colorless state by irradiating them with visible light. Dithienylethenes and fulgides are examples of photochromic molecules that generally exhibit thermal bi-stability. If the isomerization is also capable thermally (by applying heat), as is the case in spiropyrans, azabenzenes, schiff bases and the like, the molecules are classified as both thermochromic and photochromic. This is shown in the following reaction:

cyanine transient document systems) are not significantly stable and revert back to the colorless state through both thermal and visible light activation. Merocyanines can exist as various constitutional isomers due to the cis-trans isomerization about the double bond alpha to the spiro center. For steric reasons, however, only the cis form is responsible for the back reaction to the colorless state. These isomerizations are shown below:

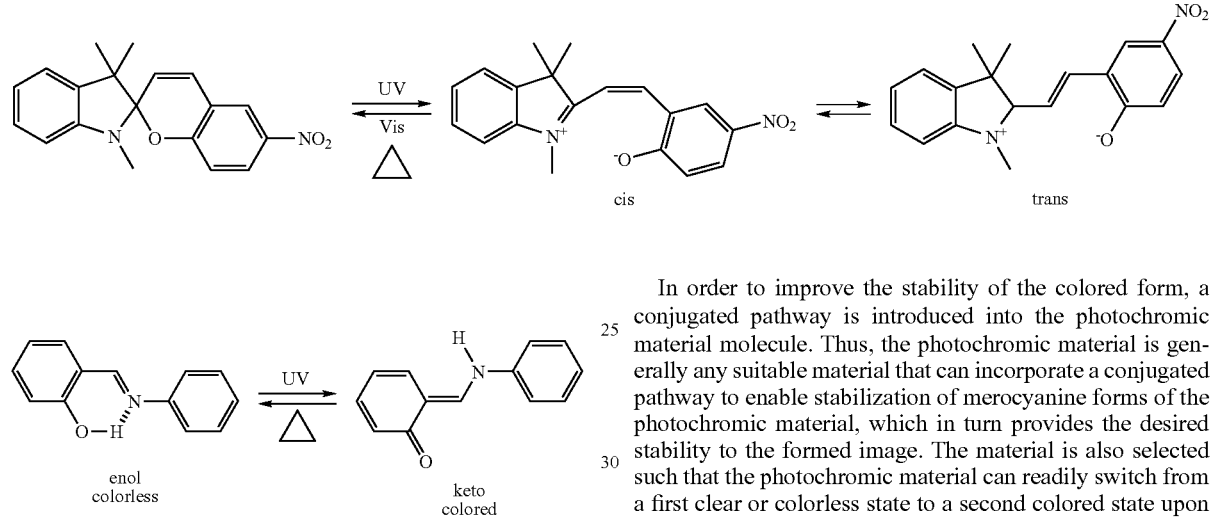

Photochromic compounds are typically bi-stable in absence of light whereas photochromic-thermochromic compounds will transform in the absence of light through a thermal process to the thermodynamically more stable state. To create a stable reimagable erase-on-demand document it is desired to stabilize the colored state, specifically to ambient conditions (light and temperature) that the document will encounter.

In embodiments, to overcome this problem, the image forming medium generally comprises an imaging layer coated on or impregnated in a suitable substrate material, or sandwiched or laminated between a first and a second substrate material (i.e., a substrate material and an overcoat layer). The imaging layer comprises an improved photochromic material having conjugated pathways that provide increased thermal stability in the colored state. The improved photochromic material is dispersed in a polymeric binder, and exhibits a reversible transition between a colorless state and a colored state in response to heat and light.

The photochromic material in embodiments is an improved photochromic material having lengthened conjugated pathways for example with respect to typical spiropyran and spirooxazines for increased thermal stability. Thus, for example, the photochromic material has at least one set of two or more conjugated double bonds in the molecule, and can have two or more sets of two or more conjugated double bonds in the molecule, as desired. In embodiments, at least one of the double bonds is alpha to the spiro center of the spiropyran compound. These conjugated double bonds impart significantly improved stability to the merocyanine forms of the photochromic material, and particularly the colored ionic forms.

By way of explanation, common merocyanines (the isomer responsible for creating image contrast in spiropyran/mero- In order to improve the stability of the colored form, a conjugated pathway is introduced into the photochromic material molecule. Thus, the photochromic material is generally any suitable material that can incorporate a conjugated pathway to enable stabilization of merocyanine forms of the photochromic material, which in turn provides the desired stability to the formed image. The material is also selected such that the photochromic material can readily switch from a first clear or colorless state to a second colored state upon exposure to light such as UV light, and can readily switch from the second colored state back to the first clear or colorless state upon suitable exposure to light such as visible light and optionally heat. The color state change in embodiments is reversible, and thus the image can be "erased" and the image forming medium returned to a blank state.

In embodiments, any suitable composition can be used for forming the imaging layer. For example, the imaging layer can comprise the photochromic material having conjugated pathways for increased thermal stability, dispersed in a polymeric binder. The active imaging materials can be dispersed in any suitable medium for forming the imaging layer, such as being dispersed in a solvent, a solution, a polymer binder, or the like; provided in the form of microencapsulated materials; incorporated in an enclosed matrix to hold the imaging composition in place; and the like. However, in embodiments, the active imaging materials are provided such that they form a solid imaging layer on a substrate. In embodiments, the image forming reaction can be reversible an almost unlimited number of times, because the isomerization changes between the clear and colored states do not consume the materials over time.

The photochromic material may exhibit photochromism, which is a reversible transformation of a chemical species induced in one or both directions by absorption of an electromagnetic radiation between two forms having different absorption spectra. The first form is thermodynamically stable and may be induced by absorption of light such as ultraviolet light to convert to a second form. The second form in embodiments is stable. The reverse reaction from the second form to the first form may occur, for example, thermally, or by absorption of light such as visible light, or both. Various exemplary embodiments of the photochromic material may also encompass the reversible transformation of the chemical species among three or more forms in the event it is possible that reversible transformation occurs among more than two forms. The photochromic material of embodiments may be composed of one, two, three, four, or more different types of photochromic materials, each of which has reversibly inter-convertible forms. As used herein, the term "photochromic material" refers to all molecules of a specific species of the photochromic material, regardless of their temporary isomeric forms. For example, where the photochromic material is of the species spiropyran, which exhibits isomeric forms as spiropyran and merocyanine, at any given moment the molecules of the photochromic material may be entirely spiropyran, entirely merocyanine, or a mixture of spiropyran and merocyanine. In various exemplary embodiments, for each type of photochromic material, one form may be colorless or weakly colored and the other form may be differently colored.

The photochromic material may be any suitable photochromic material that is useful in providing photochromic paper including, for example, organic photochromic materials, that have conjugated pathways for increased thermal stability. Examples of photochromic materials that can be modified to include conjugated pathways include spiropyrans and related compounds like spirooxazines, spiro-naphthoxazines and thiospiropyrans. In general, spirocyclic photochromes can be structurally modified to incorporate alkene (c=c) functionalities into the spirocyclic ring system, making a larger ring system in the closed (colorless form) and an increased conjugated pathway in the colored merocyanine form. Additional examples include, for example, naphthopyrans and spirodihydroindolizines. These materials generally undergo heterocyclic cleavage to form the ring open isomer forms.

Specific examples of photochromic materials include modified spiropyrans of the formula:

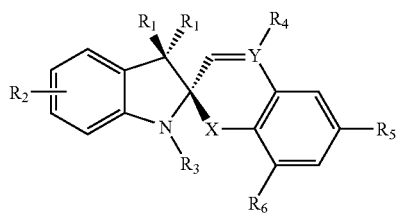

In this formula, each of $R_1$-$R_6$ independently represents any suitable group including but not limited to hydrogen; alkyl, such as methyl, ethyl, propyl, butyl, and the like, including cyclic alkyl groups, such as cyclopropyl, cyclohexyl, and the like, and including unsaturated alkyl groups, such as vinyl ($H_2C=CH-$), allyl ($H_2C=CH-CH_2-$), propynyl ($HC\equiv C-CH_2-$), and the like, where for each of the foregoing, the alkyl group has from 1 to about 50 or more carbon atoms, such as from 1 to about 30 carbon atoms; aryl, including phenyl, naphthyl, phenanthrene, anthracene, substituted groups thereof, and the like, and having from about 6 to about 30 carbon atoms such as from about 6 to about 20 carbon atoms; arylalkyl, such as having from about 7 to about 50 carbon atoms such as from about 7 to about 30 carbon atoms; silyl groups; nitro groups; cyano groups; halide atoms, such as fluoride, chloride, bromide, iodide, and astatide; amine groups, including primary, secondary, and tertiary amines; hydroxy groups; alkoxy groups, such as having from 1 to about 50 carbon atoms such as from 1 to about 30 carbon atoms; aryloxy groups, such as having from about 6 to about 30 carbon atoms such as from about 6 to about 20 carbon atoms; alkylthio groups, such as having from 1 to about 50 carbon atoms such as from 1 to about 30 carbon atoms; arylthio groups, such as having from about 6 to about 30 carbon atoms such as from about 6 to about 20 carbon atoms; aldehyde groups; ketone groups; ester groups; amide groups; carboxylic acid groups; sulfonic acid groups; and the like. The alkyl, aryl, and arylalkyl groups can also be substituted with groups such as, for example, silyl groups; nitro groups; cyano groups; halide atoms, such as fluoride, chloride, bromide, iodide, and astatide; amine groups, including primary, secondary, and tertiary amines; hydroxy groups; alkoxy groups, such as having from 1 to about 20 carbon atoms such as from 1 to about 10 carbon atoms; aryloxy groups, such as having from about 6 to about 20 carbon atoms such as from about 6 to about 10 carbon atoms; alkylthio groups, such as having from 1 to about 20 carbon atoms such as from 1 to about 10 carbon atoms; arylthio groups, such as having from about 6 to about 20 carbon atoms such as from about 6 to about 10 carbon atoms; aldehyde groups; ketone groups; ester groups; amide groups; carboxylic acid groups; sulfonic acid groups; and the like. X is a heteroatom, such as N, O, and S. However, some compounds matching the above general formula may not be photochromic, and thus are not encompassed by the present disclosure (whether particular compounds are photochromic can be readily assessed through routine experimentation). For example, where each of $R_1$ and $R_3$ is methyl, $R_2$ is hydrogen, and both $R_5$ and $R_6$ are nitro ($-NO_2$) groups, the resultant compound is not photochromic, presumably due to a decrease in the electron density on the oxygen atom under the influence of the $NO_2$ groups, coupled with the extended conjugation. See, for example, Chunaev, Yu. M. et al. Chem. Heterocycl. Compd., 628 (1984). In the above formula, Y represents an alkene group of from 3 to about 15 carbon atoms and provides at least one conjugated double bond to the double bond of the parent molecule.

Specific examples of such modified spiropyrans include those of the formula:

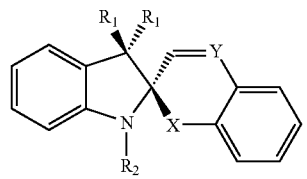

where each of $R_1$, $R_2$, and $R_3$ and X and Y are defined as above. Y can be $-N-$ or $-CH-$ in typical spirooxazine and spiropyran compounds respectively. However, to provide the conjugate pathway, Y in embodiments represents an alkene group of from 3 to about 15 carbon atoms or more, and provides at least one conjugated double bond to the double bond of the parent molecule. Thus, for example, to provide a single conjugated double bond Y can represent $C-C=C$, to provide two conjugated double bonds Y can represent $C-C=C-C=C$ or $C-C=C-C=C-C=C$ or the like, and so forth. The Y group can also be substituted or unsubstituted in a main chain or pendant to the chain, such as by including a heteroatom such as N in the chain (such as being $C-C=C-N$, $C-C=C-C=C-N$, $C-C=C-N-C=C-C=C$, $C-C=C-C=C-C=C-N$, or the like).

Other examples of suitable compounds include those of the formulae:

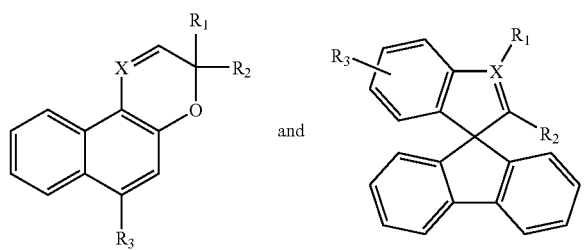

where each of $R_1$, $R_2$, and $R_3$ are defined as above, and X is an alkene group of from 3 to about 15 carbon atoms and provides at least one conjugated double bond to the double bond of the parent molecule.

If desired, the above photochromic materials may also be modified, for example, by including additional functional groups. For example, suitable functional groups that can be added to the photochromic material include, but are not limited to, silyl, nitro, cyano, halide atoms, amine, hydroxyl, alkoxy, aryloxy, alkylthio, arylthio, aldehyde, ketone, ester, amide, $SO_3H$ groups, carboxylic acid ($CO_2H$) groups, $CONR_2$ groups (where the R groups can be the same or different), $CO_2R$ groups, sulfonamide groups, and the like. The sulfonamide groups can also be unsubstituted ($SO_2NH_2$) or substituted ($SO_2NR_2$, where the R groups can include H, alkyl, aryl, arylalkyl groups and the like as described above for the photochromic materials, and can be the same or different). In another embodiment, sulfonic acid salts (—$SO_3M$) and carboxylic acid salts (COOM) can be suitable functional groups for achieving precipitation of the colored isomer. In these salts, M represents a positive counter ion and can be, for example, metal ions such as $Na^+$, $Li^+$, $Mg^{2+}$, $Ca^{2+}$, $Al^{3+}$, $Zn^{2+}$, $Cu^+$, $Cu^{2+}$ as well as ammonium ions of the general formula, $R^4N^+$ ions where R represents organic radicals that can be identical or different. Such functional groups can be readily incorporated into the photochromic materials by known processes. In some embodiments, the functional group is a carboxylic acid group (—COOH).

Because the trans isomers of these photochromic materials are more stable than the cis isomers, and because alkenes with increased conjugation pathways are energetically more stable than their less conjugated counterparts, it is believed that incorporation of the conjugation pathways into the photochromic materials helps drive the photochromic materials to more stable isomeric forms. The introduction of an additional merocyanine double bond in direct conjugation with the first alkene would yield a much longer lived merocyanine colored state as a result of stabilization due to extended conjugation in the trans-trans state. Furthermore, from molecular modeling it is believed that only the cis-cis form is capable of revision back to the colorless state, which can only be achieved by cycling through additional states, such as the cis-trans and/or the trans-cis constitutional isomers. For example, the following scheme shows the various transition states of a photochromic material according to the present disclosure:

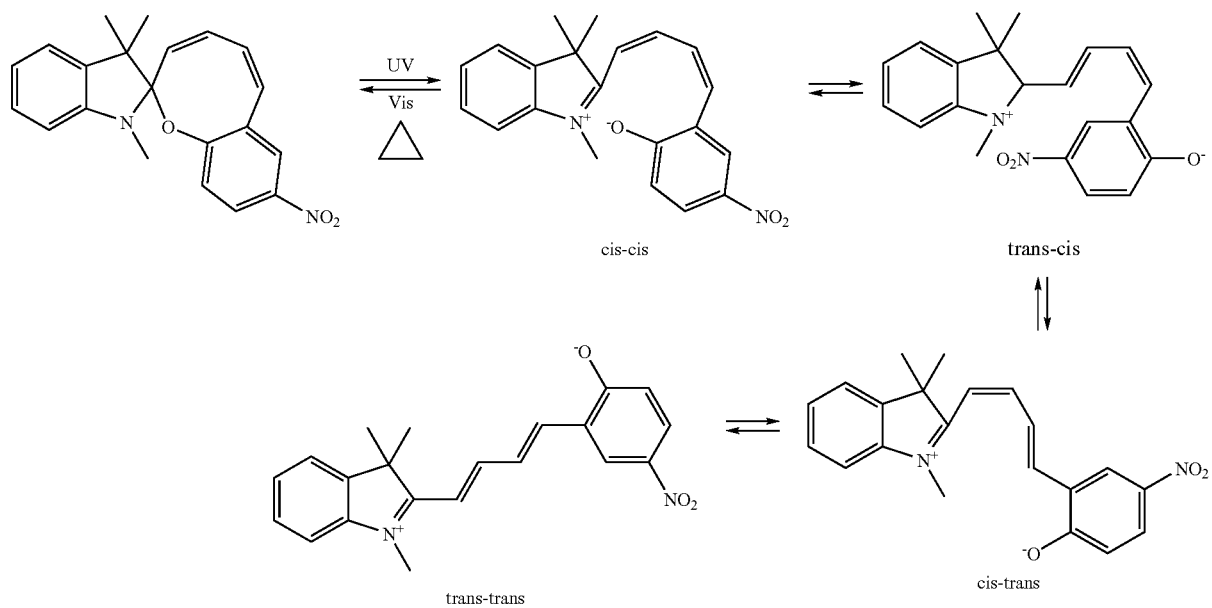

An additional feature of the photochromic material including a conjugated pathway, in embodiments, is that the type and size of conjugated pathway can affect the color of the colored ionic state. Thus, for example, whereas a conventional spiropyran tends to exhibit a purple colored state, a spiropyran having two conjugated double bonds tends to exhibit a dark blue to black colored state. In embodiments this is desirable because the blue colored tends more closely approximates blue or black ink, colors more end-users are familiar with.

Photochromic materials including a conjugated pathway can be produced by any suitable process known in the art for introducing conjugations into organic molecules, or for modifying molecules to include conjugations. For example, the photochromic material can be synthesized in three steps overall from commercially available starting materials. As one exemplary example, the photochromic material is the scheme immediately above can be prepared as follows. The first step is a standard Wittig reaction in the presence of excess base (1), followed by acid induced deprotection of the acetal to yield the conjugated aldehyde (2). The product is produced by coupling Fischer's base to 2 to yield spiropyran 3. This is shown in the following reaction:

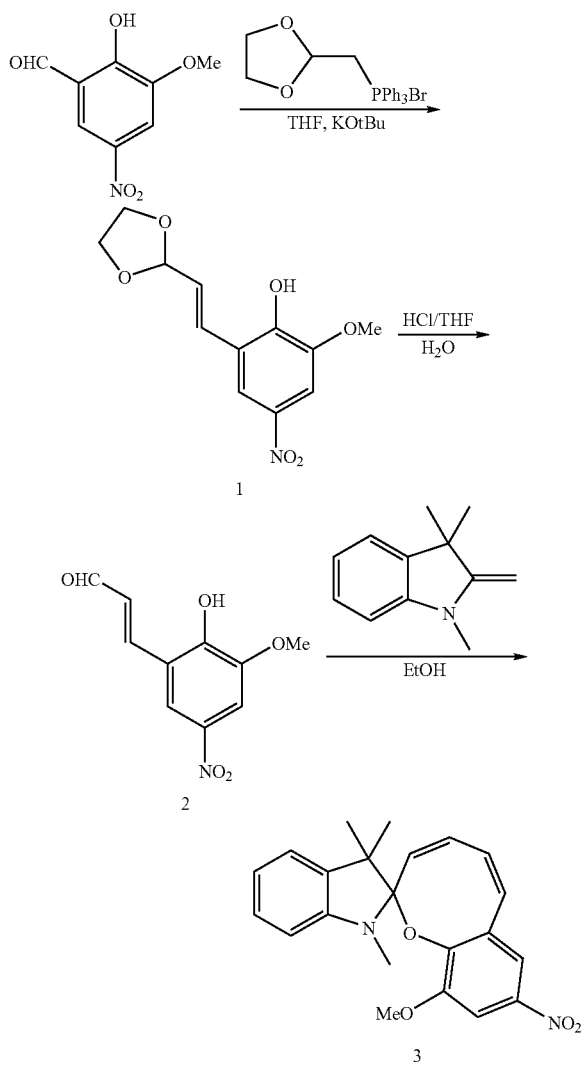

Additional details of such syntheses can be found, for example, in J. Chem. Soc., Perkin Trans. 1974, 1, 37; J. Am. Chem. Soc., 1959, 81, 5605; and Syn. Commun., 2000, 30, 5, 895, the entire disclosures of which are incorporated herein by reference.

The image forming materials (photochromic material) are dispersed in any suitable carrier, such as solvent, an additional polymer binder, or the like. Suitable examples of polymer binders include, but are not limited to, polyalkylacrylates like polymethyl methacrylate (PMMA), polycarbonates, polyethylenes, oxidized polyethylene, polypropylene, polyisobutylene, polystyrenes, poly(styrene)-co-(ethylene), polysulfones, polyethersulfones, polyarylsulfones, polyarylethers, polyolefins, polyacrylates, polyvinyl derivatives, cellulose derivatives, polyurethanes, polyamides, polyimides, polyesters, silicone resins, epoxy resins, polyvinyl alcohol, polyacrylic acid, and the like. Copolymer materials such as poly-styrene-acrylonitrile, polyethylene-acrylate, vinylidenechloride-vinylchloride, vinylacetate-vinylidene chloride, styrene-alkyd resins are also examples of suitable binder materials. The copolymers may be block, random, or alternating copolymers. In some embodiments, polymethyl methacrylate or a polystyrene is the polymer binder, in terms of their cost and wide availability.

Phase change materials can also be used as the polymer binder. Phase change materials are known in the art, and include for example crystalline polyethylenes such as Polywax® 2000, Polywax® 1000, Polywax® 500, and the like from Baker Petrolite, Inc.; oxidized wax such as X-2073 and Mekon wax, from Baker-Hughes Inc.; crystalline polyethylene copolymers such as ethylene/vinyl acetate copolymers, ethylene/vinyl alcohol copolymers, ethylene/acrylic acid copolymers, ethylene/methacrylic acid copolymers, ethylene/carbon monoxide copolymers, polyethylene-b-polyalkylene glycol wherein the alkylene portion can be ethylene, propylene, butylenes, pentylene or the like, and including the polyethylene-b-(polyethylene glycol)s and the like; crystalline polyamides; polyester amides; polyvinyl butyral; polyacrylonitrile; polyvinyl chloride; polyvinyl alcohol hydrolyzed; polyacetal; crystalline poly(ethylene glycol); poly(ethylene oxide); poly(ethylene terephthalate); poly(ethylene succinate); crystalline cellulose polymers; fatty alcohols; ethoxylated fatty alcohols; and the like, and mixtures thereof.

In embodiments, the imaging composition can be applied in one form, and dried to another form for use. Thus, for example, the imaging composition comprising photochromic material and binder polymer may be dissolved or dispersed in a solvent for application to or impregnation into a substrate, with the solvent being subsequently evaporated to form a dry layer.

In general, the imaging composition can include the imaging material and carrier (polymer binder) in any suitable amounts, such as from about 5 to about 99.5 percent by weight carrier, such as from about 30 to about 70 percent by weight carrier, and from about 0.05 to about 50 percent by weight each of photochromic material, such as from about 0.1 to about 5 percent each of photochromic material.

For applying the imaging layer to the image forming medium substrate, the image forming layer composition can be applied in any suitable manner. For example, the image forming layer composition can be mixed and applied with any suitable solvent or polymer binder, and subsequently hardened or dried to form a desired layer. Further, the image forming layer composition can be applied either as a separate distinct layer to the supporting substrate, or it can be applied so as to impregnate into the supporting substrate.

The image forming medium may comprise a supporting substrate, coated or impregnated on at least one side with the imaging layer. As desired, the substrate can be coated or impregnated on either only one side, or on both sides, with the imaging layer. When the imaging layer is coated or impregnated on both sides, or when higher visibility of the image is desired, an opaque layer may be included between the supporting substrate and the imaging layer(s) or on the opposite side of the supporting substrate from the coated imaging layer. Thus, for example, if a one-sided image forming medium is desired, the image forming medium may include a supporting substrate, coated or impregnated on one side with the imaging layer and coated on the other side with an opaque layer such as, for example, a white layer. Also, the image forming medium may include a supporting substrate, coated or impregnated on one side with the imaging layer and with an opaque layer between the substrate and the imaging layer. If a two-sided image forming medium is desired, then the image forming medium may include a supporting substrate, coated or impregnated on both sides with the imaging layer, and with at least one opaque layer interposed between the two coated imaging layers. Of course, an opaque supporting substrate, such as conventional paper, may be used in place of a separate supporting substrate and opaque layer, if desired.

Any suitable supporting substrate may be used. For example, suitable examples of supporting substrates include, but are not limited to, glass, ceramics, wood, plastics, paper, fabrics, textile products, polymeric films, inorganic substrates such as metals, and the like. The plastic may be for example a plastic film, such as polyethylene film, polyethylene terephthalate, polyethylene naphthalate, polystyrene, polycarbonate, polyethersulfone. The paper may be, for example, plain paper such as XEROX® 4024 paper, ruled notebook paper, bond paper, silica coated papers such as Sharp Company silica coated paper, Jujo paper, and the like. The substrate may be a single layer or multi-layer where each layer is the same or different material. In embodiments, the substrate has a thickness ranging for example from about 0.3 mm to about 5 mm, although smaller or greater thicknesses can be used, if desired.

When an opaque layer is used in the image forming medium, any suitable material may be used. For example, where a white paper-like appearance is desired, the opaque layer may be formed from a thin coating of titanium dioxide, or other suitable material like zinc oxide, inorganic carbonates, and the like. The opaque layer can have a thickness of, for example, from about 0.01 mm to about 10 mm, such as about 0.1 mm to about 5 mm, although other thicknesses can be used.

If desired, a further overcoating layer may also be applied over the applied imaging layer. The further overcoating layer may, for example, be applied to further adhere the underlying layer in place over the substrate, to provide wear resistance, to improve appearance and feel, and the like. The overcoating layer can be the same as or different from the substrate material, although in embodiments at least one of the overcoating layer and substrate layer is clear and transparent to permit visualization of the formed image. The overcoating layer can have a thickness of, for example, from about 0.01 mm to about 10 mm, such as about 0.1 mm to about 5 mm, although other thicknesses can be used. For example, if desired or necessary, the coated substrate can be laminated between supporting sheets such as plastic sheets.

In embodiments where the imaging material is coated on or impregnated into the substrate, the coating can be conducted by any suitable method available in the art, and the coating method is not particularly limited. For example, the imaging material can be coated on or impregnated into the substrate by dip coating the substrate into a solution of the imaging material composition followed by any necessary drying, or the substrate can be coated with the imaging composition to form a layer thereof. Similarly, the protective coating can be applied by similar methods.

In its method aspects, the present disclosure involves providing an image forming medium comprised of a substrate and an imaging layer comprising as a photochromic material a spiropyran compound having a conjugated pathway, dispersed in a polymeric binder, which composition can be provided as a dry coating onto or into the substrate. To provide separate writing and erasing processes, imaging is conducted by applying a first stimulus, such as UV light irradiation, to the imaging material to cause a color change, and erasing is conducted by applying a second, different stimulus, such as UV or visible light irradiation, and optionally heat, to the imaging material to reverse the color change. Thus, for example, the imaging layer as a whole could be sensitive at a first (such as UV) wavelength that causes the photochromic material to convert from a clear to a colored state, while the imaging layer as a whole could be sensitive at a second, different (such as visible) wavelength that causes the photochromic material to convert from the colored back to the clear state.

In embodiments, heating can be applied to the imaging layer before or at the same time as the light irradiation, for either the writing and/or erasing processes. However, in embodiments, heating is not required for the writing process, as such stimuli as UV light irradiation are sufficient to cause the color change from colorless to colored and the formation of the desired stable isomeric forms, while heating may be desired for the erasing process to assist in increasing material mobility for speeding the color change from colored to colorless and the reversal of the isomerization changes. When used, the heat raises the temperature of the imaging composition, particularly the photochromic material, to raise the mobility of the imaging composition and thus allow easier and faster conversion from one color state to the other. The heating can be applied before or during the irradiation, if the heating causes the imaging composition to be raised to the desired temperature during the irradiation. Any suitable heating temperature can be used, and will depend upon, for example, the specific imaging composition used. For example, the heating can be conducted to raise the polymer binder to at or near its glass transition temperature or melting point, such as within about 5° C., within about 10° C., or within about 20° C. of the glass transition temperature or melting point, although it is desired in certain embodiments that the temperature not exceed the melting point so as to avoid undesired movement or flow of the polymer materials on the substrate.

The different stimuli, such as different light irradiation wavelengths, can be suitably selected to provide distinct writing and erasing operations. For example, in one embodiment, the photochromic material is selected to be sensitive to UV light to cause isomerization from the clear state to the colored state, but to be sensitive to visible light to cause isomerization from the colored state to the clear state. In other embodiments, the writing and erasing wavelengths are separated by at least about 10 nm, such as at least about 20 nm, at least about 30 nm, at least about 40 nm, at least about 50 nm, or at least about 100 nm. Thus, for example, if the writing wavelength is at a wavelength of about 360 nm, then the erasing wavelength is desirably a wavelength of greater than about 400 nm, such as greater than about 500 nm. Of course, the relative separation of sensitization wavelengths can be dependent upon, for example, the relatively narrow wavelengths of the exposing apparatus.

In a writing process, the image forming medium is exposed to an imaging light having an appropriate activating wavelength, such as a UV light source such as a light emitting diode (LED), in an imagewise fashion. The imaging light supplies sufficient energy to the photochromic material to cause the photochromic material to convert, such as isomerize, from a clear state to a colored state to produce a colored image at the imaging location, and for the photochromic material to isomerize to stable isomer forms to lock in the image. The amount of energy irradiated on a particular location of the image forming medium can affect the intensity or shade of color generated at that location. Thus, for example, a weaker intensity image can be formed by delivering a lesser amount of energy at the location and thus generating a lesser amount of colored photochromic unit, while a stronger intensity image can be formed by delivering a greater amount of energy to the location and thus generating a greater amount of colored photochromic unit. When suitable photochromic material, polymer binder, and irradiation conditions are selected, the variation in the amount of energy irradiated at a particular location of the image forming medium can thus allow for formation of grayscale images, while selection of other suitable photochromic materials can allow for formation of full color images.

Once an image is formed by the writing process, the extended conjugated isomer forms and the new photochromic materials are more stable to ambient heat and light, and thus exhibit greater long-term color stability. The image is thereby stabilized or locked in, and cannot be readily erased in the absence of a specific second stimuli. The imaging substrate thus provides a reimagable substrate that exhibits a long-lived image lifetime, but which can be erased as desired and reused for additional imaging cycles.

In an erasing process, the writing process is essentially repeated, except that a different stimuli, such as a different wavelength irradiation light, such as visible light, is used, and when the photochromic material is optionally heated such as to a temperature at or near a glass transition, melting, or boiling point temperature of the carrier material. The erasing process causes the isomerizations to reverse and the photochromic unit to convert, such as isomerize, from a colored state to a clear state to erase the previously formed image at the imaging location. The erasing procedure can be on an image-wise fashion or on the entire imaging layer as a whole, as desired. The heating step is optional, in that certain compositions can be provided that are erased upon only exposure to the selected stimulus such as light wavelength, while other compositions can be provided that are more robust or thermally stable and can be erased only upon exposure to the selected stimulus such as light wavelength under a heating condition.

The separate imaging lights used to form the transient image and erase the transient image may have any suitable predetermined wavelength scope such as, for example, a single wavelength or a band of wavelengths. In various exemplary embodiments, the imaging lights are an ultraviolet (UV) light and a visible light each having a single wavelength or a narrow band of wavelengths. For example, the UV light can be selected from the UV light wavelength range of about 200 nm to about 475 nm, such as a single wavelength at about 365 nm or a wavelength band of from about 360 nm to about 370 nm. For forming the image, as well as for erasing the image, the image forming medium may be exposed to the respective imaging or erasing light for a time period ranging from about 10 milliseconds to about 5 minutes, particularly from about 30 milliseconds to about 1 minute. The imaging and erasing light may have an intensity ranging from about 0.1 mW/cm$^2$ to about 100 mW/cm$^2$, particularly from about 0.5 mW/cm$^2$ to about 10 mW/cm$^2$.

In various exemplary embodiments, imaging light corresponding to the predetermined image may be generated for example by a computer or a Light Emitting Diode (LED) array screen and the image is formed on the image forming medium by placing the medium on or in proximity to the LED screen for the desired period of time. In other exemplary embodiments, a UV Raster Output Scanner (ROS) may be used to generate the UV light in an image-wise pattern. This embodiment is particularly applicable, for example, to a printer device that can be driven by a computer to generate printed images in an otherwise conventional fashion. That is, the printer can generally correspond to a conventional inkjet printer, except that the inkjet printhead that ejects drops of ink in the imagewise fashion can be replaced by a suitable UV light printhead that exposes the image forming medium in an imagewise fashion. In this embodiment, the replacement of ink cartridges is rendered obsolete, as writing is conducted using a UV light source. Other suitable imaging techniques that can be used include, but are not limited to, irradiating a UV light onto the image forming medium through a mask, irradiating a pinpoint UV light source onto the image forming medium in an imagewise manner such as by use of a light pen, and the like.

For erasing an image in order to reuse the imaging substrate, in various exemplary embodiments, the substrate can be exposed to a suitable imaging light, to cause the image to be erased. Such erasure can be conducted in any suitable manner, such as by exposing the entire substrate to the erasing light at once, exposing the entire substrate to the erasing light in a successive manner such as by scanning the substrate, or the like. In other embodiments, erasing can be conducted at particular points on the substrate, such as by using a light pen, or the like.

According to various exemplary implementations, the color contrast that renders the image visible to an observer may be a contrast between, for example two, three or more different colors. The term "color" may encompass a number of aspects such as hue, lightness and saturation, where one color may be different from another color if the two colors differ in at least one aspect. For example, two colors having the same hue and saturation but are different in lightness would be considered different colors. Any suitable colors such as, for example, red, white, black, gray, yellow, cyan, magenta, blue, and purple, can be used to produce a color contrast as long as the image is visible to the naked eye of a user. However, in terms of desired maximum color contrast, a desirable color contrast is a dark gray or black image on a light or white background, such as a gray, dark gray, or black image on a white background, or a gray, dark gray, or black image on a light gray background.

In various exemplary embodiments, the color contrast may change such as, for example, diminish during the visible time, but the phrase "color contrast" may encompass any degree of color contrast sufficient to render an image discernable to a user regardless of whether the color contrast changes or is constant during the visible time.

An example is set forth hereinbelow and is illustrative of different compositions and conditions that can be utilized in practicing the disclosure. All proportions are by weight unless otherwise indicated. It will be apparent, however, that the disclosure can be practiced with many types of compositions and can have many different uses in accordance with the disclosure above and as pointed out hereinafter.

EXAMPLES

Example 1

A spirocyclic compound ((3Z,5Z)-1',3',3'-trimethyl-8-nitrospiro[benzo[b]oxocine-2,2'-indoline] containing an enlarged spirocyclic heterocycle is prepared as described previously having the following structure and molecular formula $C_{21}H_{20}N_2O_3$:

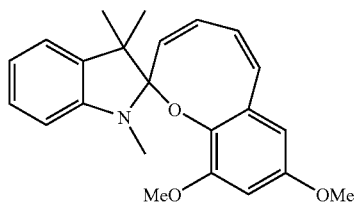

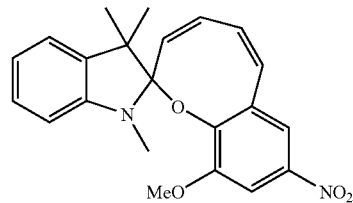

A toluene solution of (3Z,5Z)-8,10-dimethoxy-1',3',3'-trimethylspiro[benzo[b]oxocine-2,2'-indoline] and polymethylmethacrylate (PMMA) is prepared at 3 wt %. The solution is then coated onto Xerox 4024 paper and allowed to dry. The document is printed or written by exposing desired areas to UV light (365 nm) creating the conjugated and colored extended merocyanine isomers. The document is stable in the colored state for an extended period of time (up to several days). Erasing can be achieved by heating the paper (>80° C.), such as by passing is through a printer's fuser system and or exposing the paper to visible light.

Example 2

A spirocyclic compound (3Z,5Z)-8-methoxy-1',3',3'-trimethylspiro[benzo[b]oxocine-2,2'-indoline] containing an enlarged spirocyclic heterocycle is prepared as described previously having the following structure and molecular formula $C_{22}H_{23}NO_2$:

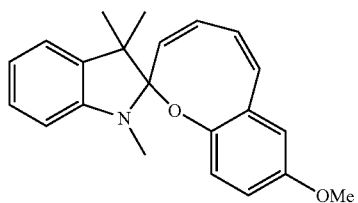

A toluene solution of (3Z,5Z)-8-methoxy-1',3',3'-trimethylspiro[benzo[b]oxocine-2,2'-indoline] and polymethylmethacrylate (PMMA) is prepared at 3 wt %. The solution is then coated onto Xerox 4024 paper and allowed to dry. The document is printed or written by exposing desired areas to UV light (365 nm) creating the conjugated and colored extended merocyanine isomers. The document is stable in the colored state for an extended period of time (up to several days). Erasing can be achieved by heating the paper (>80° C.), such as by passing is through a printer's fuser system and or exposing the paper to visible light.

Example 3

A spirocyclic compound (3Z,5Z)-10-methoxy-1',3',3'-trimethyl-8-nitrospiro[benzo[b]oxocine-2,2'-indoline] containing an enlarged spirocyclic heterocycle is prepared as described previously having the following structure and molecular formula $C_{22}H_{22}N_2O_4$:

A toluene solution of (3Z,5Z)-10-methoxy-1',3',3'-trimethyl-8-nitrospiro[benzo[b]oxocine-2,2'-indoline] and polymethylmethacrylate (PMMA) is prepared at 3 wt %. The solution is then coated onto Xerox 4024 paper and allowed to dry. The document is printed or written by exposing desired areas to UV light (365 nm) creating the conjugated and colored extended merocyanine isomers. The document is stable in the colored state for an extended period of time (up to several days). Erasing can be achieved by heating the paper (>80° C.), such as by passing is through a printer's fuser system and or exposing the paper to visible light.

It will be appreciated that various of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

What is claimed is:

1. A photochromic compound having a conjugated pathway, the photochromic compound having the formula (1), (2), or (3):

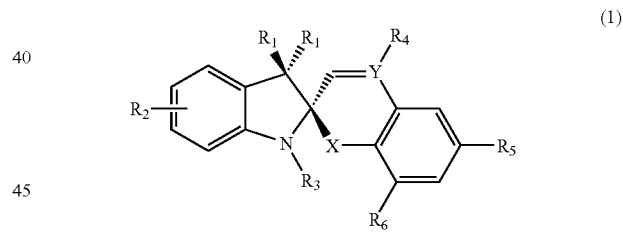

wherein:
  each of $R_1$-$R_6$ independently represents a group selected from the group consisting of hydrogen, alkyl, aryl, arylalkyl, silyl, nitro, cyano, halide atoms, amine, hydroxyl, alkoxy, aryloxy, alkylthio, arylthio, aldehyde, ketone, ester, amide, carboxylic acid, and sulfonic acid, wherein the alkyl, aryl, and arylalkyl groups can optionally be substituted with one or more groups selected from the group consisting of silyl groups, nitro groups, cyano groups, halide atoms, amine groups, hydroxy groups, alkoxy groups, aryloxy groups, alkylthio groups, arylthio groups, aldehyde groups, ketone groups, ester groups, amide groups, carboxylic acid groups, and sulfonic acid groups,
  X is a heteroatom selected from the group consisting of N, O, and S, and
  Y represents an alkene group of from 3 to about 15 carbon atoms and provides at least one conjugated double bond to a double bond of the parent molecule;

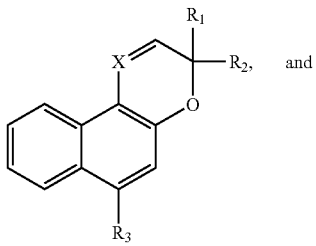

(2)

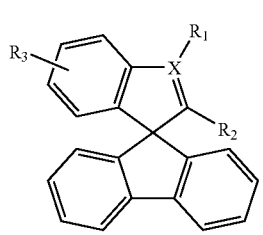

(3)

where each of $R_1$, $R_2$, and $R_3$ are defined as above, and X in formulae (2) and (3) is an alkene group of from 3 to about 15 carbon atoms and provides at least one conjugated double bond to the double bond of the parent molecule.

2. The photochromic compound of claim 1, wherein each of $R_1$-$R_6$ is selected from the group consisting of hydrogen, methyl, ethyl, propyl, butyl, cyclopropyl, cyclohexyl, vinyl, allyl, propynyl, phenyl, naphthyl, phenanthrene, anthracene, silyl, nitro, cyano, fluoride, chloride, bromide, iodide, astatide, amine, hydroxyl, aldehyde, ketone, ester, amide, carboxylic acid, and sulfonic acid.

3. The photochromic compound of claim 1, wherein Y is selected from the group consisting of C—C=C, C—C=C—C=C, C—C=C—C=C—C=C, C—C=C—N, C—C=C—C=C—N, C—C=C—N—C=C—C=C, and C—C=C—C—C=C—C=C—N.

4. The photochromic compound of claim 1, wherein the photochromic compound is a compound of formula (1).

5. The photochromic compound of claim 1, wherein the photochromic compound is a compound of formula (2).

6. The photochromic compound of claim 1, wherein the photochromic compound is a compound of formula (3).

7. An image forming medium, comprising
a substrate; and
an imaging layer coated on or impregnated into said substrate, the imaging layer comprising as a photochromic material a spiropyran compound having a conjugated pathway, dispersed in a polymeric binder,
wherein:
the photochromic material exhibits a reversible transition between a colorless state and a colored state in response to heat and light; and
the spiropyran compound is selected from the group consisting of compounds having the formula (1), (2), and (3):

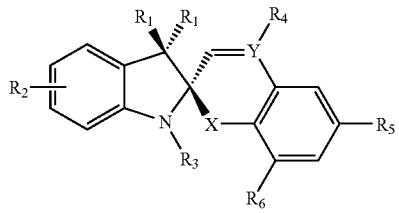

(1)

wherein:
each of $R_1$-$R_6$ independently represents a group selected from the group consisting of hydrogen, alkyl, aryl, arylalkyl, silyl, nitro, cyano, halide atoms, amine, hydroxyl, alkoxy, aryloxy, alkylthio, arylthio, aldehyde, ketone, ester, amide, carboxylic acid, and sulfonic acid, wherein the alkyl, aryl, and arylalkyl groups can optionally be substituted with one or more groups selected from the group consisting of silyl groups, nitro groups, cyano groups, halide atoms, amine groups, hydroxy groups, alkoxy groups, aryloxy groups, alkylthio groups, arylthio groups, aldehyde groups, ketone groups, ester groups, amide groups, carboxylic acid groups, and sulfonic acid groups, X is a heteroatom selected from the group consisting of N, O, and S, and Y represents an alkene group of from 3 to about 15 carbon atoms and provides at least one conjugated double bond to the double bond of the parent molecule;

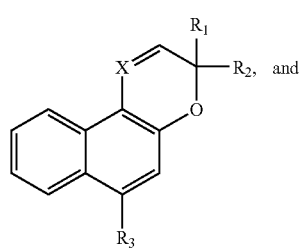

(2)

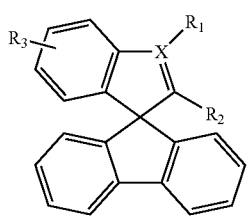

(3)

wherein each of $R_1$, $R_2$, and $R_3$ are defined as above, and X in formulae (2) and (3) is an alkene group of from 3 to about 15 carbon atoms and provides at least one conjugated double bond to the double bond of the parent molecule.

8. The image forming medium of claim 7, wherein the spiropyran compound is selected from the group consisting of spirooxazines, spiro-naphthoxazines and thiospiropyrans.

9. The image forming medium of claim 7, wherein Y is selected from the group consisting of C—C=C, C—C=C—

C=C, C—C=C—C—C=C—C=C, C—C=C—N, C—C=C—C=C—N, and C—C=C—C=C—C=C—N.

10. The image forming medium of claim 7, wherein the spiropyran compound has one pair of conjugated double bonds, wherein one of the double bonds is alpha to the spiro center.

11. The image forming medium of claim 7, wherein the spiropyran compound has two or more pairs of conjugated double bonds, wherein one of the double bonds is alpha to the spiro center.

12. The image forming medium of claim 7, wherein the photochromic material comprises at least one functional group selected from the group consisting of $SO_3H$, COOH, $CONR_2$, $CO_2R$, COX, $SO_2X$, $SO_2NH_2$, $SO_2NR_2$, $R_4N^+$, $SO_3M$, and COOM, wherein the R groups can be the same or different and represent H, alkyl, aryl, or arylalkyl groups having from 1 to about 50 carbon atoms; X is a halogen; and M represents a positive metal counter ion.

13. The image forming medium of claim 7, wherein the colored state of the photochromic material is provided by the spiropyran compound being in a trans-trans isomeric form.

14. The image forming medium of claim 7, wherein the polymeric binder is selected from the group consisting of polyalkylacrylates, polycarbonates, polyethylenes, oxidized polyethylene, polypropylene, polyisobutylene, polystyrenes, poly(styrene)-co-(ethylene), polysulfones, polyethersulfones, polyarylsulfones, polyarylethers, polyolefins, polyacrylates, polyvinyl derivatives, cellulose derivatives, polyurethanes, polyamides, polyimides, polyesters, silicone resins, epoxy resins, polyvinyl alcohol, polyacrylic acid, polystyrene-acrylonitrile, polyethylene-acrylate, vinylidenechloride-vinylchloride, vinylacetate-vinylidene chloride, styrene-alkyd resins, and mixtures thereof.

15. The image forming medium of claim 7, wherein the photochromic material is present in an amount of from about 0.01% to about 20% by weight of a total dry weight of the imaging layer.

16. The image forming medium of claim 7, wherein the substrate is selected from the group consisting of glass, ceramic, wood, plastic, paper, fabric, textile, metals, plain paper, and coated paper.

17. A method of making an image forming medium, comprising applying an imaging layer composition to a substrate, wherein:
the imaging layer composition comprises as a photochromic material a spiropyran compound having a conjugated pathway, dispersed in a polymeric binder;
the photochromic material exhibits a reversible transition between a colorless state and a colored state in response to heat and light; and
the spiropyran compound is selected from the group consisting of compounds having the formula (1), (2), and (3):

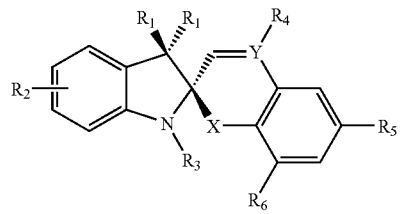

(1)

wherein:
each of $R_1$-$R_6$ independently represents a group selected from the group consisting of hydrogen, alkyl, aryl, arylalkyl, silyl, nitro, cyano, halide atoms, amine, hydroxyl, alkoxy, aryloxy, alkylthio, arylthio, aldehyde, ketone, ester, amide, carboxylic acid, and sulfonic acid, wherein the alkyl, aryl, and arylalkyl groups can optionally be substituted with one or more groups selected from the group consisting of silyl groups, nitro groups, cyano groups, halide atoms, amine groups, hydroxy groups, alkoxy groups, aryloxy groups, alkylthio groups, arylthio groups, aldehyde groups, ketone groups, ester groups, amide groups, carboxylic acid groups, and sulfonic acid groups.

X is a heteroatom selected from the group consisting of N, O, and

Y represents an alkene group of from 3 to about 15 carbon atoms and provides at least one conjugated double bond to the double bond of the parent molecule;

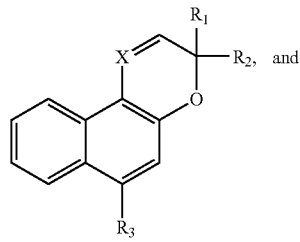

(2)

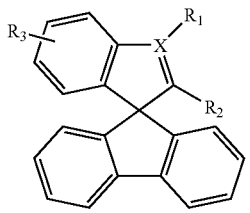

(3)

wherein each of $R_1$, $R_2$, and $R_3$ are defined as above, and X in formulae (2) and (3) is an alkene group of from 3 to about 15 carbon atoms and provides at least one conjugated double bond to the double bond of the parent molecule.

18. The method of claim 17, wherein the applying comprises coating the imaging layer over the substrate or impregnating the imaging layer into the substrate.

19. A method of forming an image, comprising:
providing an image forming medium comprising:
a substrate; and
an imaging layer coated on or impregnated into said substrate, the imaging layer comprising as a photochromic material a spiropyran compound having a conjugated pathway, dispersed in a polymeric binder; and
exposing the image forming medium to UV irradiation of a first wavelength in an imagewise manner to form a visible image,
wherein:
the photochromic material exhibits a reversible transition between a colorless state and a colored state in response to heat and light; and
the spiropyran compound is selected from the group consisting of compounds having the formula (1), (2), and (3);

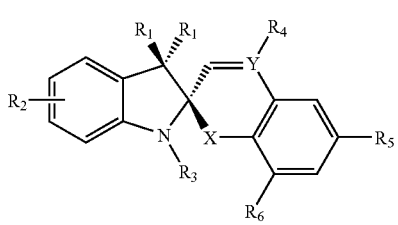

(1)

wherein:
each of $R_1$-$R_6$ independently represents a group selected from the group consisting of hydrogen, alkyl, aryl, arylalkyl, silyl, nitro, cyano, halide atoms, amine, hydroxyl, alkoxy, aryloxy, alkylthio, arylthio, aldehyde, ketone, ester, amide, carboxylic acid, and sulfonic acid, wherein the alkyl, aryl, and arylalkyl groups can optionally be substituted with one or more groups selected from the group consisting of silyl groups, nitro groups, cyano groups, halide atoms, amine groups, hydroxy groups, alkoxy groups, aryloxy groups, alkylthio groups, arylthio groups, aldehyde groups, ketone groups, ester groups, amide groups, carboxylic acid groups, and sulfonic acid groups.
X is a heteroatom selected from the group consisting of N, O, and S, and
Y represents an alkene group of from 3 to about 15 carbon atoms and provides at least one conjugated double bond to the double bond of the parent molecule;

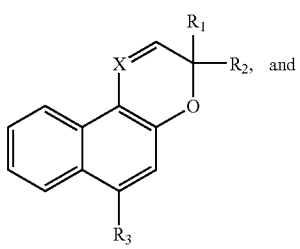

(2)

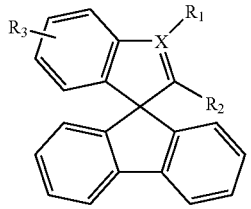

(3)

wherein each of $R_1$, $R_2$, and $R_3$ are defined as above, and X in formulae (2) and (3) is an alkene group of from 3 to about 15 carbon atoms and provides at least one conjugated double bond to the double bond of the parent molecule.

20. The method of claim 19, further comprising:
exposing the image forming medium bearing said image to light irradiation of a second wavelength in an imagewise manner, optionally while heating the photochromic material, wherein said light irradiation causes said photochromic material to change from the colored state to the colorless state; and repeating the step of exposing the image forming medium to the UV irradiation of a first wavelength in an imagewise manner at least one additional time.

21. The method of claim 19, wherein the exposing is for a time period ranging from about 10 milliseconds to about 5 minutes at an intensity ranging from about 0.1 mW/cm² to about 100 mW/cm².

22. An imaging system, comprising:
the image forming medium of claim 7;
a printer comprising two irradiation sources, wherein one irradiation source sensitizes the photochromic material to convert the photochromic material from a colorless state to a colored state the other irradiation source converts the photochromic material from a colored state to a colorless state.

23. An image forming medium, comprising
a substrate; and
an imaging layer coated on or impregnated into said substrate, the imaging layer comprising as a photochromic material a spiropyran compound having a conjugated pathway, dispersed in a polymeric binder,
wherein:
the photochromic material exhibits a reversible transition between a colorless state and a colored state in response to heat and light; and
the spiropyran compound has two or more pairs of conjugated double bonds, wherein one of the double bonds is alpha to the spiro center.

* * * * *